United States Patent [19]
Pees

[11] Patent Number: 5,985,883
[45] Date of Patent: Nov. 16, 1999

[54] FUNGICIDAL TRICHLOROPHENYL-TRIAZOLOPYRIMIDINES

[75] Inventor: Klaus-Juergen Pees, Mainz, Germany

[73] Assignee: American Cyanamid Company, Madison, N.J.

[21] Appl. No.: 09/160,568

[22] Filed: Sep. 25, 1998

[51] Int. Cl.[6] .................. C07D 487/04; A01N 43/54
[52] U.S. Cl. .................. 514/258; 544/263; 544/118; 540/600; 514/212; 514/253; 514/254; 514/233.2
[58] Field of Search .............. 544/263; 514/258, 514/212, 250; 540/600

[56] References Cited

U.S. PATENT DOCUMENTS

| | | | |
|---|---|---|---|
| 4,567,263 | 1/1986 | Eicken et al. | 544/263 |
| 5,593,996 | 1/1997 | Pees et al. | 514/258 |
| 5,765,509 | 5/1998 | Pees | 514/258 |
| 5,817,663 | 10/1998 | Pees et al. | 544/263 |

*Primary Examiner*—Mukund J. Shah
*Assistant Examiner*—Ann M. Kessinger
*Attorney, Agent, or Firm*—Joseph M. Mazzarese

[57] ABSTRACT

The novel compounds of formula I:

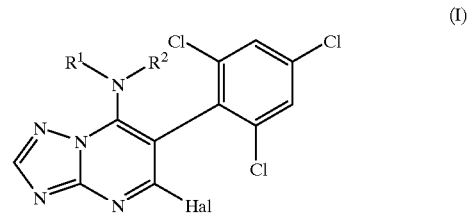

($R^1$, $R^2$ and Hal are defined in the specification) show selective fungicidal activity, in particular against rice blast disease. The new compounds are processed with carriers, and optionally an adjuvant, to make fungicidal compositions.

10 Claims, No Drawings

FUNGICIDAL TRICHLOROPHENYL-TRIAZOLOPYRIMIDINES

BACKGROUND OF THE INVENTION

This invention relates to certain trichlorophenyl-triazolopyrimidine compounds, a process for their preparation, compositions containing such compounds, a method for combating a fungus at a locus comprising treating the locus with such compounds and their use as fungicides.

EP-A-0071792 claims compounds of the general formula

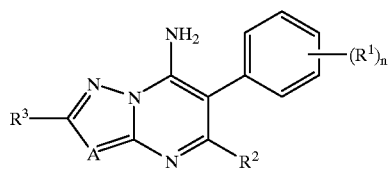

in which $R^1$ represents alkyl, halogen, alkoxy, cyano, cycloalkyl, aryl, aryloxy, arylthio, aralkyl, arylthio, arylalkyl, arylalkyloxy or arylalkylthio each optionally substituted by halogen or alkoxy; or $(R^1)_n$ represents a benzene, indane or tetrahydronaphthalene ring fused with the phenyl ring, aromatic moieties in the above groups being optionally substituted by alkyl, alkoxy, halogen or cyano; n is 1 or 2; $R^2$ and $R^3$ are each hydrogen, alkyl or aryl, A represents a nitrogen atom or a $CR^4$ group, and $R^4$ is as $R^2$ but can also be halogen, cyano or alkoxycarbonyl or together with $R^3$ can form an alkylene chain containing up to two double bonds. The compounds are said to be active against various phytopathogenic fungi, especially those of the phycomycete class. However evidence of fungicidal activity is only provided for these compounds against *Plasmo para viticola*, a member of the oomycete class of fungi. U.S. Pat. No. 5,593,996 embraces compounds of the general formula

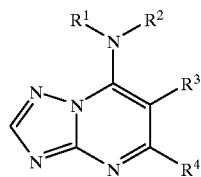

in which $R^1$ represents an optionally substituted alkyl, alkenyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted aryl group; and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen atom or an alkyl group. Thus, compounds in which $R^3$ is a trichlorophenyl group are generally covered by this patent application. These compounds are said to be active against fungi which are members of the ascomycetes class such as *Venturia inaequalis* and of the hyphomycetes class such as *Alternaria solani* and *Botrytis cinerea*. However, there is no single compound disclosed in which $R^3$ is a 2,4,6-trichlorophenyl group.

SUMMARY OF THE INVENTION

The present invention provides a compound of formula I

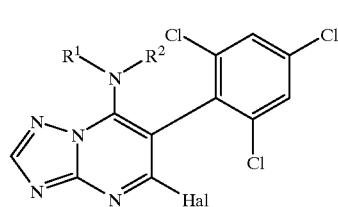

in which
$R^1$ and $R^2$ each independently represent a hydrogen atom or an optionally substituted alkyl, alkenyl, alkynyl, alkadienyl, haloalkyl, aryl, heteroaryl, cycloalkyl, bicycloalkyl or heterocyclyl group, or
$R^1$ and $R^2$ together with the interjacent nitrogen atom represent an optionally substituted heterocyclic ring, and
Hal represents a halogen atom.

The compounds of this invention show excellent fungicidal activity in various crops, in particular against *Pyricularia oryzae* (*Magnaporte grisea*) the causative agent of rice blast disease.

It is an object of the present invention to provide novel, selective fungicidal compounds.

It is also an object of the invention to provide methods for controlling an undesired fungus, in particular *Pyricularia oryzae* by contacting said plants with a fungicidally effective amount of the new compounds.

It is another object of the invention to provide fungicidal compositions containing the novel compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I

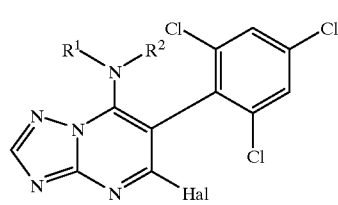

in which $R^1$, $R^2$ and Hal have the meaning given above for formula I show excellent fungicidal activity against a broad range of fungi, in particular against *Pyricularia oryzae*, the causative agent of rice blast disease.

Unless otherwise stated, as used herein the term halogen atom may denote a bromine, iodine, chlorine or fluorine atom, and is especially a bromine, chlorine or fluorine atom, in particular a chlorine atom.

Optionally substituted moieties of this invention may be unsubstituted or have from one up to the maximal possible number of substituents. Typically, 0 to 2 substituents are present.

Unless otherwise stated herein, the terms alkyl, alkenyl, alkynyl, alkadienyl as used herein with respect to a radical or moiety refer to a straight or branched chain radical or moiety having up to 10, in particular up to 6 carbon atoms. Suitably, an alkyl moiety has from 1 to 6 carbon atoms, preferably from 1 to 3 carbon atoms. A preferred alkyl moiety is an ethyl, or especially a methyl group. Suitably, an alkenyl moiety has from 2 to 6 carbon atoms. A preferred alkenyl moiety is allyl or especially a 2-methylallyl group.

The term aryl, as used herein with respect to a radical or moiety refers to an aryl group having 6, 10 or 14 carbon atoms, preferably 6 or 10 carbon atoms especially a phenyl optionally substituted by one or more halogen atoms, nitro, cyano, alkyl, preferably $C_{1-6}$ alkyl, and/or alkoxy, preferably $C_{1-6}$ alkoxy.

The term heteroaryl, as used herein, with respect to a radical or moiety refers to a heteroaryl group having 5 or 6 ring atoms selected from carbon, nitrogen, oxygen and sulphur, at least one of which is nitrogen, oxygen or sulphur.

The term cycloalkyl herein refers to a cycloalkyl group having 3 to 8 carbon atoms, preferably 5 to 7 carbon atoms, in particular cyclohexyl optionally substituted by one or more halogen atoms, nitro, cyano, alkyl, preferably $C_{1-6}$ alkyl, and/or alkoxy, preferably $C_{1-6}$ alkoxy.

The term heterocyclyl herein refers to a saturated cyclic group having 5 or 6 ring atoms selected from carbon, nitrogen, oxygen and sulphur, at least one of which is nitrogen, oxygen or sulphur, and which is optionally substituted by one or more halogen atoms, nitro, cyano, alkyl, preferably $C_{1-6}$ alkyl, and/or alkoxy, preferably $C_{1-6}$ alkoxy. Preferred heterocyclyl groups include pyrrolodinyl, pyrrazolidin, piperidinyl, piperazinyl and morpholin-4-yl.

The invention especially relates to compounds of the general formula I in which any alkyl part of the groups $R^1$ or $R^2$, which may be straight chained or branched, contains up to 9 carbon atoms, more preferably up to 6 carbon atoms, any alkenyl or alkynyl part of the substituents $R^1$ or $R^2$ contains up to 9 carbon atoms, more preferably up to 6 carbon atoms, any cycloalkyl part of the substituents $R^1$ or $R^2$ contains from 3 to 6 carbon atoms, and any aryl part of the substituent $R^1$ or $R^2$ contains 6 or 10 carbon atoms. Each optionally substituted group independently is substituted by one or more halogen atoms or nitro, cyano, hydroxy, alkyl, preferably $C_{1-6}$ alkyl, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, trialkylsilyl, preferably tri-$C_{1-4}$alkylsilyl, phenyl, halo- or dihalo-phenyl or pyridyl groups. A 4- to 6- membered heterocyclic group may have 4 to 6 ring atoms, including one or more heteroatoms selected from sulfur, nitrogen, and oxygen, preferably oxygen.

The invention especially relates to compounds of the general formula I in which $R^1$ represents a straight-chained or branched $C_{1-10}$ alkyl, in particular a branched $C_{3-10}$ alkyl group, a $C_{3-8}$ cycloalkyl, a $C_{3-8}$ cycloalkyl-$C_{1-6}$ alkyl, $C_{1-10}$ alkoxy-$C_{1-6}$ alkyl, a $C_{1-10}$ haloalkyl or a phenyl group being optionally substiuted by one to three halogen atoms or $C_{1-10}$ alkyl or $C_{1-10}$ alkoxy groups The invention especially relates to compounds of the general formula I in which $R^2$ represents a hydrogen atom, a $C_{1-10}$ alkyl or a $C_{1-10}$ haloalkyl group, in particular a hydrogen atom.

When $R^1$ is a $C_{1-10}$ haloalkyl group, preferably a polyfluorinated alkyl group, and more preferably a 2,2,2-trifluoroethyl, a 2-(1,1,1-trifluoropropyl) or a 2-(1,1,1-trifluorobutyl) group, $R^2$ preferably represents a hydrogen atom.

When $R^1$ is an optionally substituted $C_{3-8}$ cycloalkyl group, preferably a cyclopentyl or cyclohexyl group, $R^2$ preferably represents a hydrogen atom or $C_{1-6}$ alkyl group.

The invention especially relates to compounds of the general formula I in which $R^1$ and $R^2$ together with the interjacent nitrogen atom form an optionally substituted heterocyclic ring, preferably an optionally substituted $C_{3-7}$heterocyclic ring, more preferably a pyrollidine, piperidine, tetrahydropyridine, in particular 1,2,3,6-tetrahydropyridine or azepane ring which is optionally substituted by one or more $C_{1-10}$ alkyl groups.

Included in the scope of the present invention are (R) and (S) isomers of compounds of general formula I having an chiral center, the racemates thereof, and salts, N-oxides and acid addition compounds.

Fungicidal activity especially has been found in (S)-isomer compounds of general formula I wherein $R^1$ represent a chiral group of formula —CH*(R')R", wherein R' and R" represent different alkyl or haloalkyl groups.

The compounds according to general formula I may be oils, gums, or crystalline solid materials. They have valuable fungicidal properties, in particular systemicity and fungicitoxicity against rice diseases and powdery mildews. These compounds can be used in agriculture or related fields for the control of phytopathogenic fungi such as *Alternaria solani, Botrytis cinerea, Cercospora beticola, Cladosporium herbarum, Corticium rolfsii, Erysiphe graminis, Helminthosporium tritici repentis, Leptosphaeria nodorum, Micronectriella nivalis, Monilinia fructigena, Mycosphaerella ligulicola, Mycosphaerella pinodes, Pyricularia oryzae, Rhizoctonia solani* and *Sclerotinia sclerotiorum, Uncinula necator*, in particular for the control of *Pyricularia oryzae*. The compounds of formula I according to the invention possess a high fungicidal activity within a wide concentration range and may be used in agriculture without any difficulties.

Moreover, the compounds according to the invention show enhanced control of fungi, in particular of rice blast disease compared with conventional fungicides.

One preferred embodiment of the invention is a compound as defined in formula I wherein:

Hal represents a chloro atom, and $R^2$ represents a hydrogen atom.

Especially good results in terms of control of phytopathogenic fungi may be obtained by using, for example, the following compounds of formula I:

5-chloro-7-(N-but-2-ylamino)-6-(2,4,6-trichlorophenyl)-[1,2,4]triazolo[1,5-a]pyrimidine, 5-chloro-7-(N-isopropylamino)-6-(2,4,6-trichlorophenyl)-[1,2,4]triazolo[1,5-a]pyrimidine, 5-chloro-7-(3-methylpiperidin-1-yl)-6-(2,4,6-trichlorophenyl)-[1,2,4]triazolo[1,5-a]-pyrimidine, 5-chloro-7-(N-cyclopentylamino)-6-(2,4,6-trichlorophenyl)-[1,2,4]triazolo[1,5-a]pyrimidine, 5-chloro-7-(4-methylpiperidin-1-yl)-6-(2,4,6-trichlorophenyl)-[1,2,4]triazolo[1,5-a]pyrimidine, 5-chloro-7-(N,N-diethylamino)-6-(2,4,6-trichlorophenyl)-[1,2,4]triazolo[1,5-a]pyrimidine, 5-chloro-7-(N-norborn-2-ylamino)-6-(2,4,6-trichlorophenyl)-[1,2,4]triazolo[1,5-a]pyrimidine, 5-chloro-7-(N-cyclopropylamino)-6-(2,4,6-trichlorophenyl)-[1,2,4]triazolo[1,5-a]pyrimidine, 5-chloro-7-(N-2,2,2-trifluoroethylamino)-6-(2,4,6-trichlorophenyl)-[1,2,4]triazolo[1,5-a]-pyrimidine, 5-chloro-7-(N-ethyl-N-2-methylallylamino)-6-(2,4,6-trichlorophenyl)-[1,2,4]triazolo[1,5-a]pyrimidine, 5-chloro-7-[N-2-(1,1,1-trifluoropropyl)-amino]-6-(2,4,6-trichlorophenyl)-[1,2,4]triazolo[1,5-a]-pyrimidine.

The present invention further provides a process for the preparation of a compound of formula I as defined above which comprises treating a compound of the formula II

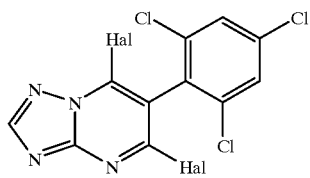
(II)

in which
Hal is as defined for formula I;
with an amine of the formula III

(III)

in which
$R^1$ and $R^2$ are as defined for formula I,
to produce a compound of formula I.

Compounds of formula II are novel, and may be prepared using known methods, such as by reacting 3-amino-1,2,4-triazole with 2-(2,4,6-trichlorophenyl)-substituted malonic acid ester of formula IV,

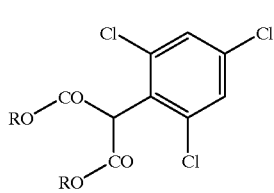
(IV)

wherein R represents alkyl, preferably $C_{1-6}$ alkyl, in particular methyl or ethyl, under alkaline conditions, preferably using high boiling tertiary amines, for example tri-n-butylamine.

The compounds of formula IV are preferably prepared by reaction of 2,4,6-trichlorobromobenzene with sodium dialkylmalonates in the presence of a copper(I) salt, e.g. by the method of J. Setsume et al. Chemistry Letters, pp. 367–370, 1981.

The resulting 5,7-dihydroxy-6-(2,4,6-trichlorophenyl)-triazolopyrimidine is subsequently treated with a halogenating agent, preferably with a brominating or chlorinating agent, such as phosphorus oxybromide or phosphorus oxychloride, neat or in the presence of a solvent. The reaction is suitably carried out at a temperature in the range from 0° C. to 150° C., the preferred reaction temperature being from 80° C. to 125° C.

Accordingly, the invention relates to the novel intermediates of formula II, in particular 5,7-dichloro-6-(2,4,6-trichlorophenyl)-([1,2,4]triazolo[1,5-a]pyrimidine, to the dialkyl (2,4,6-trichlorophenyl)-malonates of formula IV, and to the novel 5,7-dihydroxy-6-(2,4,6-trichlorophenyl)-[1,2,4] triazolo[1,5-a]pyrimidine.

The reaction between the 5,7-dihalo-6-(2,4,6-trichlorophenyl)-triazolopyrimidines of formula II and the amine of formula III is preferably carried out in the presence of a solvent. Suitable solvents include ethers, such as dioxane, diethyl ether and, especially, tetrahydrofuran, and halogenated hydrocarbons, such as dichloromethane and aromatic hydrocarbons, for example toluene. The reaction is suitably carried out at a temperature in the range from 0° C. to 70° C., the preferred reaction temperature being from 10° C. to 35° C. It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

Due to excellent activity, the compounds of formula I may be used in cultivation of all plants where infection by phytopathogenic fungi is not desired, e.g. cereals, solanaceous crops, vegetables, legumes, apples, vine.

The invention further includes a fungicidal composition, which comprises at least one compound of formula I as defined above, and one or more carriers. The invention also includes a method of making such a composition, which comprises bringing a compound of formula I into association with said carrier(s). Such a composition may contain a single active ingredient or a mixture of several active ingredients of the present invention. It is also envisaged that different isomers or mixtures of isomers may have different levels or spectra of activity, and thus, compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may, for example, be a plant, seed, soil, or water in which a plant grows, or to facilitate storage, transport or handling. A carrier may be a solid or a liquid, including material which is normally a gas but which has been compressed to form a liquid.

The compositions may be manufactured into, e.g., emulsion or emulsifiable concentrates, solutions, oil in water emulsions, wettable powders, soluble powders, suspension concentrates, dusts, granules, aerosols, water dispersible granules, micro-capsules, gels, tablets and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different solvents are often suitable.

Solid carriers, which may be used for dusts, wettable powders, water dispersible granules, or granules, may be mineral fillers, such as calcite, talc, kaolin, montmorillonite or aftapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties, depending on the nature of the compound according to formula I to be formulated. Surfactants of this invention may also include mixtures of individual surfactants.

Wettable powders suitably may contain 5 to 90% w/w of active ingredient and, in addition to solid inert carrier, 3 to 10% w/w of dispersing and wetting agents and 0 to 10% w/w of stabilizer(s) and/or other additives such as penetrants or stickers. Dusts may be formulated as a dust concentrate having a similar composition to that of a wettable powder but without a dispersant, and may be diluted in the field with further solid carrier to give a composition preferably containing 0.5 to 10% w/w of active ingredient. Water dispersible granules and granules suitably have a size between 0.15 mm and 2.0 mm, and may be manufactured by a variety of techniques. Generally, these granules contain 0.5 to 90% w/v active ingredient and 0 to 20% w/w of additives such as stabilizer, surfactants, slow release modifiers and binding agents. Emulsifiable concentrates of this invention preferably contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates may be milled to obtain a stable, non-sedimenting flowable product, and preferably contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, including compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient may be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added separately to a spray tank together with a formulation containing the active ingredient.

As a commodity, the compositions preferably may be in a concentrated form, whereas the end user generally employs diluted compositions. The compositions may be diluted to a concentration down to 0.001% of active ingredient. The doses preferably are in the range from 0.01 to 10 kg a.i./ha.

Examples of formulations according to the invention are:

| Emulsion Concentrate (EC) | | |
|---|---|---|
| Active Ingredient | Compound of Example 11 | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| Solvent | Shellsol ® A[2] (mixture of $C_9$-$C_{10}$ aromatic hydrocarbons) | to 1000 ml |
| Suspension Concentrate (SC) | | |
| Active Ingredient | Compound of Example 11 | 50% (w/v) |
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ® [5] (aqueous dipropylene glycol solution containing 20% 1,2-benisothiazoiin-3-one) | 0.1% (w/v) |
| Water | | to 1000 ml |
| Wettable powder (WP) | | |
| Active Ingredient | Compound of Example 11 | 60% (w/w) |
| Wetting agent | Atlox ® 4995[1] (polyoxyethylene alkyl ether) | 2% (w/w) |
| Dispersing agent | Witcosperse ®D-60[6] (mixture of sodium salts of condensed naphthalene sulfonic acid and alkylarylpolyoxy acetates | 3% (w/w) |
| Carrier/Filler | Kaolin | 35% (w/w) |
| Water Dispersible Granules (WG) | | |
| Active Ingredient | Compound of Example 11 | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/Filler | Kaolin | 35% (w/w) |

[1] commercially available from ICI Surfactants
[2] commercially available from Deutsche Shell AG
[3] commercially available from Rhône-Poulenc
[4] commercialiy available from Kelco Co.
[5] commercially available from Zeneca
[6] commercially available from Witco
[7] commercially available from International Speciality Products The compositions of this invention suitably may be applied to the plants or their environment simultaneously with, or in succession with, other active substances. These other active substances can be fertilisers, agents which donate trace elements, or other substances which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these substances, if appropriate, optionally together with other carrier substances conventionally used in the art of formulation, surfactants or other additives which promote application.

Furthermore, the other pesticide can have a synergistic effect on the pesticidal activity of the compound of formula I.

The other fungicidal compound can be, for example, one which is also capable of combating diseases of cereals (e.g. wheat) such as those caused by Erysipha, Puccinia, Septoria, Gibberella and Helminthospotium spp., seed and soil borne diseases, and downy and powdery mildews on vines, early and late blight on solanaceous crops, and powdery mildew and scab on apples etc. These mixtures of fungicides may have a broader spectrum of activity than the compound of formula I alone. The other fungicide may have a synergistic effect on the fungicidal activities of the compound of formula I.

Examples of other fungicidal compounds which may be used with the compounds of formula I include anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, iprovalicarb, kasugamycin, kitazin P, kresoxim-methyl, mancozeb, maneb, mepanipyrim, mepronil, metalaxyl, metconazole, methfuroxam, MON 65500 (AGROW No. 305 of May 29, 1998), myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, and ziram.

In addition, the formulations according to the invention may contain at least one compound of formula I and any of the following classes of biological control agents such as viruses, bacteria, nematodes, fungi, and other microorganisms which are suitable to control insects, weeds or plant diseases or to induce host resistance in the plants. Examples of such biological control agents are: *Bacillus thuringiensis, Verficillium lecanii, Autographica californica NPV, Beauvaria bassiana, Ampelomyces quisqualis, Bacilis subtilis, Pseudomonas chlororaphis, Pseudomonas fluorescens, Steptomyces griseoviridis* and *Trichoderma harzianum*.

Moreover, the formulations of the invention may contain at least one compound of formula I and a chemical agent that induces the systemic acquired resistance in plants such as for example nicotinic acid, or derivatives thereof, or BION.

The compounds of formula I may be mixed with soil, peat or other rooting media for the protection of the plants against seed-borne, soil-borne or foliar fungal diseases.

The invention further includes the fungicidal use of a compound of formula I or a composition thereof, and a method for combating fungus at a locus, which comprises treating the locus, which may be, for example, plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the individual compound selected, and also a variety of external factors, such as climate, the impact of which may be mitigated by the use of a suitable formulation.

The following examples further illustrate the present invention. It should be understood, however, that the invention is not limited solely to the particular examples given below.

EXAMPLE 1

Preparation of diethyl 2,4,6-trichlorophenylmalonate

Diethyl malonate (6.21 mol) is added to a mixture of sodium hydride (5.13 mol) and 1,4-dioxane (1400 ml) at 55 to 60° C. within 3 hours. The mixture is stirred for 10 minutes at 55° C. and copper(I) bromide (0.5 mol) is added. A mixture of 2,4,6-trichlorobromobenzene (2.50 mol) and 1,4-dioxane (600 ml) is added. The reaction mixture is heated at 100° C. for 14 hours and cooled to 15° C. Hydrochloric acid (12N, 350 ml) is added slowly at 15 to 20° C. The organic phase is separated off and the aqueous phase is extracted with ethyl acetate (250 ml) and toluene (200 ml). The combined organic phases are concentrated in vacuo. The residue is filtered over silica gel, washed with petroleum ether/ethyl acetate (15:1) and the solvent is distilled off. The residue is distilled in vacuo to yield 540 g of the product as a white solid, 144–150° C. at 0.4 mbar.

EXAMPLE 2

Preparation of 5,7-Dichloro-(2,4,6-trichlorophenyl)-1,2,4-triazolo[1.5a]pyrimidine A mixture of 3-amino-1,2,4-triazole (0.15 mol), diethyl 2,4,6-trichlorophenylmalonate (0.15 mol, obtained from Example 1) and tributylamine (0.15 mole) is heated at 170° C. and ethanol formed during the reaction is distilled off. Subsequently, the reaction mixture is cooled to 130° C. and phosphorous oxychloride (0.45 mol) is added within 30 minutes. The reaction mixture is heated with reflux for 6 hours. A mixture of water and toluene (1.5 l, 6:5) is added slowly.The organic phase is separated, washed with dilute hydrochloric acid and water, dried an concentrated in vacuo to yield a brown viscous oil (45 g) which contains 85% of the title product.

EXAMPLE 3

A mixture of N,N-diethylamine (1.4 mmoles), triethylamine (1.4 mmoles) and dichloromethane (10 ml) is added to a mixture of 5,7-dichloro-(2,4,6-trichlorophenyl)-1,2,4- triazolo[1.5a]pyrimidine (1.4 mmoles) and dichloromethane (30 ml) under stirring. The reaction mixture is stirred 16 hours at room temperature, subsequently washed two times with 1 N hydrochloric acid and once with water. The organic layer is separated, dried with anhydrous sodium sulphate and the solvent is evaporated under reduced pressure. Treatment of the resulting light brown oil with tert.-butyl methyl ether (50 ml) yields beige crystals having a melting point of 199–201° C.

EXAMPLES 4–13

The following examples (Table I; structure and melting point) are synthesized analogously to Example 3.

TABLE I

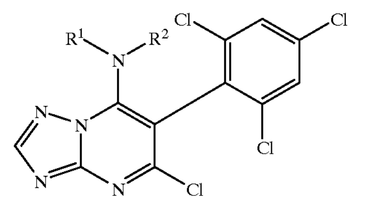

| Example | $R^1$ | $R^2$ | melting point (° C.) |
|---|---|---|---|
| 4 | 2-butyl | H | oil |
| 5 | iso-propyl | H | oil |
| 6 | $—CH_2—CH(CH_3)—(CH_2)_3—$ | | oil |
| 7 | cyclopentyl | H | 160 |
| 8 | $—(CH_2)_2—CH(CH_3)—(CH_2)_2—$ | | 220 |
| 9 | norborn-2-yl | H | 155 |
| 10 | cyclopropyl | H | oil |
| 11 | 2,2,2-trifluoroethyl | H | oil |
| 12 | 2-methylallyl | ethyl | |
| 13 | 1,1,1-trifluoroprop-2-yl | H | |

Biological Investigations

Determination of Minimum Inhibitory Concentration by Test Compounds in the Serial Dilution Test with *Pyricularia grisea f. sp. Oryzae*

The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 μg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min.

The inocula of *Pyricularis oryzae*, PYRIOR; are added into the wells as spore suspensions (50 ml; $5\times10^5$/ml) or agar slices (6 mm) of an agar culture of the fungus.

After 6–12 days incubation at suitable temperatures (18–25° C.), the MIC values are determined by visual inspection of the plates (Table II; n. t.=not tested).

TABLE II

| Example No. | MIC [μg/ml] |
|---|---|
| 3 | 0.10 |
| 4 | 1.56 |
| 5 | 0.39 |
| 6 | 0.10 |
| 7 | 0.20 |
| 8 | 0.10 |
| 9 | 0.39 |
| 10 | 1.56 |
| 11 | 0.04 |

What is claimed is:

1. A compound of formula I (I)

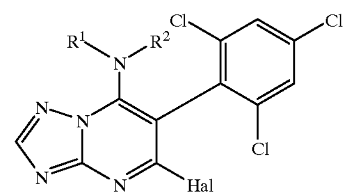

in which $R^1$ represents straight chained or branched $C_1$–$C_6$-alkyl, $C_1$–$C_6$-haloalkyl or straight chained or branched $C_2$–$C_6$-alkenyl, a $C_3$–$C_8$-cycloalkyl or a norborn-2-yl group, and $R^2$ represents hydrogen or $C_1$–$C_6$-alkyl, or $R^1$ and $R^2$ together with the interjacent nitrogen atom represent a heterocyclic ring with 5 or 6 carbon atoms being optionally substituted with one or two $C_1$–$C_6$-alkyl groups, and Hal represents a halogen atom.

2. A compound according to claim 1 in which $R^2$ represents a hydrogen atom.

3. A compound according to claim 1 in which $R^1$ and $R^2$ together with the interjacent nitrogen atom represent a heterocyclic ring selected from 4-methylpiperidin-1-yl, 2-ethylpiperidin-1-yl, 5,6-dihydro-2H-pyridin-1-yl, 2-ethylpiperidin-1-yl and azepan-1-yl.

4. A compound according to claim 1 selected from the group consisting of:

5-chloro-7-(N-but-2-ylamino)-6-(2,4,6-trichlorophenyl)-[1,2,4]triazolo[1,5-a]pyrimidine;

5-chloro-7-(N-isopropylamino)-6-(2,4,6-trichlorophenyl)-[1,2,4]triazolo[1,5-a]pyrimidine;

5-chloro-7-(3-methylpiperidin-1 -yl)-6-(2,4,6-trichlorophenyl)-[1,2,4]triazolo[1,5-a]pyrimidine;

5-chloro-7-(N-cyclopentylamino)-6-(2,4,6-trichlorophenyl)-[1,2,4]triazolo[1,5-a]pyrimidine;

5-chloro-7-(4-methylpiperidin-1 -yl)-6-(2,4,6-trichlorophenyl)-[1,2,4]triazolo[1,5-a]pyrimidine;

5-chloro-7-(N,N-diethylamino)-6-(2,4,6-trichlorophenyl)-[1,2,4]triazolo[1,5-a]pyrimidine;

5-chloro-7-(N-norborn-2-ylamino)-6-(2,4,6-trichlorophenyl)-[1,2,4]triazolo[1,5-a]pyrimidine;

5-chloro-7-(N-cyclopropylamino)-6-(2,4,6-trichlorophenyl)-[1,2,4]triazolo[1,5-a]pyrimidine;

5-chloro-7-(N-2,2,2-trifluoroethylamino)-6-(2,4,6-trichlorophenyl)-[1,2,4]triazolo[1,5-a]pyrimidine;

5-chloro-7-(N-ethyl-N-2-methylallylamino)-6-(2,4,6-trichlorophenyl)-[1,2,4]triazolo[1 ,5-a]pyrimidine; and, 5-chloro-7-[N-2-(1,1,1-trifluoropropyl)-amino]-6-(2,4,6-trichlorophenyl)-[1,2,4]triazolo[1,5-a]pyrimidine.

5. A process for the preparation of a compound of formula I as defined in claim 1 which comprises treating a compound of formula II

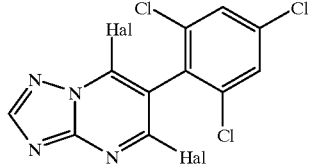
(II)

in which

Hal is a halogen atom, with an amine of formula III

(III)

in which $R^1$ and $R^2$ are as defined in claim 1.

6. A compound of formula II

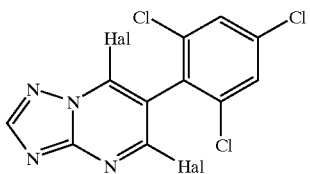
(II)

in which

Hal is a halogen atom.

7. 5,7-Dihydroxy-6-(2,4,6-trichlorophenyl)-[1,2,4]triazolo[1,5-a]pyrimidine.

8. A fungicidal composition which comprises a carrier, and as active agent, at least one compound of formula I as defined in claim 1.

9. A method of combating fungus at a locus which comprises treating the locus with a compound of formula I as defined in claim 1.

10. The method according to claim 9 wherein the fungus is *Pyricularia oryzae*.

* * * * *